United States Patent [19]

Hart et al.

[11] Patent Number: 6,083,741
[45] Date of Patent: Jul. 4, 2000

[54] INTERNALISATION OF DNA, USING CONJUGATES OF POLY-L-LYSINE AND AN INTEGRIN RECEPTOR LIGAND

[75] Inventors: Stephen L. Hart; Richard P. Harbottle, both of London, United Kingdom

[73] Assignee: Imperial College of Science Technology and Medicine, London, United Kingdom

[21] Appl. No.: 08/836,786

[22] PCT Filed: Nov. 17, 1995

[86] PCT No.: PCT/GB95/02706

§ 371 Date: May 16, 1997

§ 102(e) Date: May 16, 1997

[87] PCT Pub. No.: WO96/15811

PCT Pub. Date: May 30, 1996

[30] Foreign Application Priority Data

Nov. 17, 1994 [GB] United Kingdom ............... 9423231
Nov. 18, 1994 [GB] United Kingdom ............... 9423306
Jun. 23, 1995 [GB] United Kingdom ............... 9512622

[51] Int. Cl.$^7$ ................... C12N 15/63; C12N 15/11; C07K 5/00; C07K 14/00
[52] U.S. Cl. ................... 435/320.1; 536/23.1; 530/330; 530/317; 530/378; 530/333; 530/350
[58] Field of Search ............... 514/44; 530/300, 530/317, 328, 333, 350; 536/23.1; 435/320.1

[56] References Cited

FOREIGN PATENT DOCUMENTS

WO94/18834  1/1994  WIPO .

OTHER PUBLICATIONS

J. Biol Chem, Apr. 5, 1987, vol. 262, No. 10, pp. 4429–4432, Wu Gy et al, "Receptor–mediated in vitro gene transformation by a soluble DNA carrier system"& J Biol Chem, 1988 Jan. 5, vol. 263, No. 1, p. 588, "published erratum" L: provided for complete information.

Biochemistry, Feb. 9 1988, vol. 27, No. 3, pp. 887–892, Wu Gy et al, "Evidence for targeted gene delivery to Hep G2 hepatoma cells in vitro.".

Proc. Natl Acad. Sci. U.S.A.A., 1991, vol. 88, No. 19, pp. 8850–8854, US, Curiel D.T. et al, "Adenovirus enhancement of transferrin–polylysine–mediated gene delivery".

Neurology, Apr. 1994, vol. 44, No. 4 Suppl. 2, p. A268, Abstract No. 567S, XP 000562694 Ascade G et al, "Optimization of in vivo gene transfer into skeletal muscle cells by adenovirus vector" & 46th Annual Meeting of the American Academy of Cuerology, Washington, D.C., USA, May 1–7, 1994.

Ann, New York Adac. Sci., 1994, vol. 716, pp. 36–58, US, XP 000452729 Curiel D.T. et al, "High–efficiency gene transfer mediated by adenovirus–polylysine–DNA complexes".

Keystone Symposium on Gene Therapy and Molecular Medicine, Steamboat Springs, Colorado, US, Mar. 26–Apr. 1, 1995. Published In: Journal of Cellular Biochemistry, Supplement 21A, 1995, p. 394, Abstract No. C6–321, Harbottle R et al, "RGD–mediated gene delivery and expression in epithelial cells".

Cotten, M. et al, "Receptor–mediated transport of DNA into eukaryotic cells", Methods Enzymol., 1993, vol. 217, Part H, pp. 618–644, USA XP 000562730.

J. Biol. Chem., 29-4-1994, vol. 269, No. 17, pp. 12468–1247, USA, Hart S.L. et al, "Cell binding and internalization by filamentous phage displaying a cyclic Arg–Gly–Asp–containing peptide".

EMBO J., 1993, vol. 12, No. 5, pp. 1887–1895, Oxford, GB, Van Nhieu G.T. et al, "Bacterial internalization mediated by beta1 chain integrins is determined by ligand affinity and receptor density".

Chemical Abstracts, vol. 122, No. 21, May 22, 1995, Columbus, Ohio, US; abstract No. 262311, Isberg, Ralph R., "Internalization of microbial pathogens by integrin receptors and the binding of the Yersinia pseudotuberculosis invasin protein" & Integrins Biol. Probl. 1994, pp. 197–216. Editor(s): Takada, Yoshizaku., 1994 Boca Raton, US.

Database WPI, Section Ch, Week 9238, Derwent Publications Ltd., London, GB; Class B04, AN 92–313681 & JP,A,04 221 397 (Fuji Photo Film Co Ltd), Aug. 11, 1992 & Chemical Abstracts, vol. 118, No. 21, May 24, 1993 Columbus, Ohio, US; abstract No. 213547, p. 972; col. 1; & Patent Abstracts of Japan vol. 16 No. 566 (C–1009), Dec. 8, 1992.

Cell, 1993, vol. 73, No. 2, pp. 309–319, 1993 Cambridge, US, Wickham, Thomas J. et al, "Integrins.alpha.v.beta.3 and.alpha.v.beta.5 promote adenovirus internalization but not virus attachment".

J. Biol. Chem., vol. 269, No. 32, pp. 20233–20238, Aug. 12, 1994, Pfaff, Martin et al, "Selective recognition of cyclic RGD peptides of NMR defined conformation by.alpha.IIb-.beta.3,.alpha.V.beta.3, and.alpha.5.beta.1 integrins".

Trends in Microbiology, 1994, vol. 2, No. 1, pp. 10–14., XP 000562727 Isberg R R et al, "Binding and internalization of microorganisms by integrin receptors".

Nat. Immun., vol. 13, No. 2–3, pp. 141–164, Mar. 1994–Jun. 1994, Basel, CH, XP 000562731, Curiel D.T., "High–efficiency gene transfer employing Adenovirus–polylysine–DNA complexes".

(List continued on next page.)

*Primary Examiner*—Bruce R. Campell
*Assistant Examiner*—AnneMarie S. Beckerleg
*Attorney, Agent, or Firm*—Nixon & Vanderhye P.C.

[57] ABSTRACT

Composition comprising DNA associated with a polycation moiety wherein the polycation moiety is itself coupled to an integrin receptor binding moiety is disclosed. Preferably, the integrin receptor binding moiety is a peptide, and the compositions can be used to deliver DNA to a cell where it will be expressed, for example, to treat a condition by gene therapy. In a preferred embodiment, the integrin receptor binding moiety comprises a peptide, in particular a cyclic peptide, comprising the sequence RGD. In a particularly preferred embodiment, the peptide comprises the sequence GGCRGDMFGC. Cyclic configuration in this sequence is imposed by virtue of the presence of two cysteine residues which can form a disulphide bond.

30 Claims, 6 Drawing Sheets

OTHER PUBLICATIONS

Exp. Cell Res., 1992, vol. 199, No. 2, pp. 323–329, XP 000562696 Rosenkranz A.A. et al, "Receptor–mediated endocytosis and nuclear transport of a transfecting DNA construct".

Journal of Biological Chemistry, 1993, vol. 268, No. 15, pp. 11265–11271., Chowdury N R et al, "Fate of DNA Targeted to the Liver by Asialoglycoprotein Receptor–Mediated Endocytosis In–Vivo Prolonged Persistence in Cytoplasm Vesicles After Partial Hepatectomy".

Stephen Hart, et al.; "Cell Binding and Internalization by Filamentous Phage Displaying a Cyclic Arg–Gly–Asp–containing Peptide"; Apr. 29, 1994; *Jour. of Biological Chemistry*; vol. 269, No. 17, pp. 12468–12474.

Ralph Isberg; "Discrimination Between Intracellular Uptake and Surface Adhesion of Bacterial Pathogens"; May 17, 1991; *Science*; vol. 252; pp. 934–938.

David Relman, et al.; "Recognition of a Bacterial Adhesin by an Integrin: Macrophage CR3 ($\alpha_M\beta_2$, CD11b/CD18) Blinds Filamentous Hemagglutinin of Bordetella pertussis"; Jun. 29, 1990; *Cell*; vol. 61, pp. 1375–1382.

Matt Cotton, et al.; "Transferrin–polycation–mediated introduciton of DNA into human leukemic cells: Stimulation by agents that affect the survival of transfected DNA or modulate transferrin receptor levels"; Jun., 1990; *Proc. Natl. Acad. Sci.*; vol. 87; pp. 4033–4037.

Hart et al. (Apr. 1994) J. Biol. Chem., vol. 269 (17) 12468–12474.

Miller et al. (Feb. 1995) FASEB, vol. 9, 190–199.

Marshall. E. (Aug. 1995) Science, vol. 269, 1050–1055.

Orkin et al. (Dec. 1995) "Report and Recommendations of the Panel to Assess the NIH Investment in Research on Gene Therapy".

Verma et al. (Sep. 1997) Nature, vol. 389, 239–242.

Rosenkranz et al. (1992) Exp. Cell Res., vol. 199, 323–329.

Doherty et al. (Jan. 1990) J. Cell Biol., vol. 110, 35–42.

CYCLIC RGD-CONTAINING PEPTIDE ATTACHED TO A POLYCATION

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 3 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Arg Gly Asp
1

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Gly Gly Cys Arg Gly Asp Met Phe Gly Cys
1               5                   10

(2) INFORMATION FOR SEQ ID NO:3:

(i) SEQUENCE CHARACTERISTICS:
      (A) LENGTH: 26 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Gly Gly Cys Arg Gly Asp Met Phe Gly Cys Lys Lys Lys Lys Lys Lys
1               5                   10                  15

Lys Lys Lys Lys Lys Lys Lys Lys Lys Lys
            20                  25

(2) INFORMATION FOR SEQ ID NO:4:

(i) SEQUENCE CHARACTERISTICS:
      (A) LENGTH: 27 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:4:

-continued

```
Lys Lys Lys Lys Lys Lys Lys Lys Lys Lys Lys Lys Lys Lys Lys Lys
1               5                   10                  15

Gly Gly Cys Arg Cys Asp Met Phe Gly Cys Ala
            20                  25
```

INTERNALISATION OF DNA, USING CONJUGATES OF POLY-L-LYSINE AND AN INTEGRIN RECEPTOR LIGAND

This is a Continuation of PCT application PCT/GB95/02706, filed Nov. 17, 1995.

The present invention relates to compositions comprising DNA associated with a polycation entity which is itself linked to an integrin specific binding moiety. The compositions of the invention can be used to deliver DNA to cells for internalisation and expression therein. In particular, therefore, the invention relates to methods of obtaining gene expression in cells to overcome genetic deficiencies.

In recent years, with the continuing identification of specific genes responsible for certain disease conditions, the concept of "gene therapy" has attracted a great deal of attention. The potential to deliver a new gene, or even part of a gene sequence, to a defective cell in order to correct such an inherent deficiency is an attractive one. There are, of course, inherent problems in such an approach. For instance, the DNA must be delivered in a form that will be taken up, or internalised, by the target cell. Furthermore, the DNA itself must be expressed effectively in the cell in order to overcome the genetic deficiency. Inherent in these problems is the additional one that the DNA itself, after having entered the cell, must be protected in some way to prevent its damage, or even destruction, by, for example, cellular enzymes.

One potential approach to this problem of internalisation, and protection, of DNA is disclosed in Hart et al (*J. Biol. Chem.*, 269, No 176: 12468–12474 (1994)). This approach exploits the presence of integrin receptors on cell surfaces for achieving internalisation of filamentous phage. Integrins are a super family of heterodimeric cell adhesion molecules that consist of several different α an β subunits. Their cellular function is to mediate the movement, shape and polarity of cells through binding with proteins of the extracelluar matrix. In addition, integrins are exploited as receptors for cell entry by pathogenic bacteria, such as *Yersinia pseudotuberculosis* (Isberg, R., *Science*, 252: 934–938 (1991)) and *Bordatella pertussis* (Relamna et al, *Cell*, 61: 1375–1382 (1990)).

Hart et al (supra) found that displaying an integrin-binding peptide sequence on the surface of bacteriophage fD particles enabled the phage particles to be internalised by mammalian cells. However, no effective expression of DNA carried by phage particles was shown.

In addition, there are certain problems associated with the use of such particles to deliver DNA in this fashion. Firstly, there is a packaging size limitation governed by the size of the phage particle itself. Only genetic material up to a particular particle size could be delivered in this fashion. Secondly, the phage itself will only package single stranded genetic material, and this would not be effectively expressed in a mammalian cell system. Finally, the phage itself consists of other proteins and is a somewhat "messy" system for delivering DNA. It is possible that these additional components would have a material effect on whether or not genetic material was expressed.

Other approaches to delivering DNA into mammalian cells are disclosed in WO-A-9418834. Here, DNA was conjugated with a polyelectrolyte to form a complex which was then inserted into an embryonic cell, a germ cell or a germ precursor cell. This method was disclosed primarily for producing transgenic animals. The methods disclosed in this document rely on either microinjection of the complex directly into the germ cell, or by having the polycation/DNA complex present in the culture medium and relying on uptake by the cells.

Cotton et al (*PNAS USA*, 87: 4033–4037 (1990)) used the natural iron-delivery protein transferrin, coupled to DNA binding polycations such as polylysine or protamine, to deliver DNA into human leukaemic cells. However, they also found that they required the use of other agents to effect the survival of the transfected DNA or to modulate transferrin receptor levels so as to increase the internalisation or uptake of the DNA itself. These steps included increasing the transferring receptor density through treatment of the cells with the cell-permeable ion chelator, desferioxamine, interfering with the synthesis of heme with succinol acetone treatment or stimulating the degradation of heme with cobalt chloride treatment. In other words, effective uptake and expression of the DNA could only be achieved through the use of "co-factors" or co-treatments.

SUMMARY OF THE INVENTION

Thus, there exists a need for further and better methods of delivering DNA to a cell such that it will be internalised and expressed efficiently therein, preferably without the need for any other co-factors or co-treatments, and in a form which is not limited to genetic material of a particular size.

DETAILED DESCRIPTION OF THE INVENTION

Figure 1:
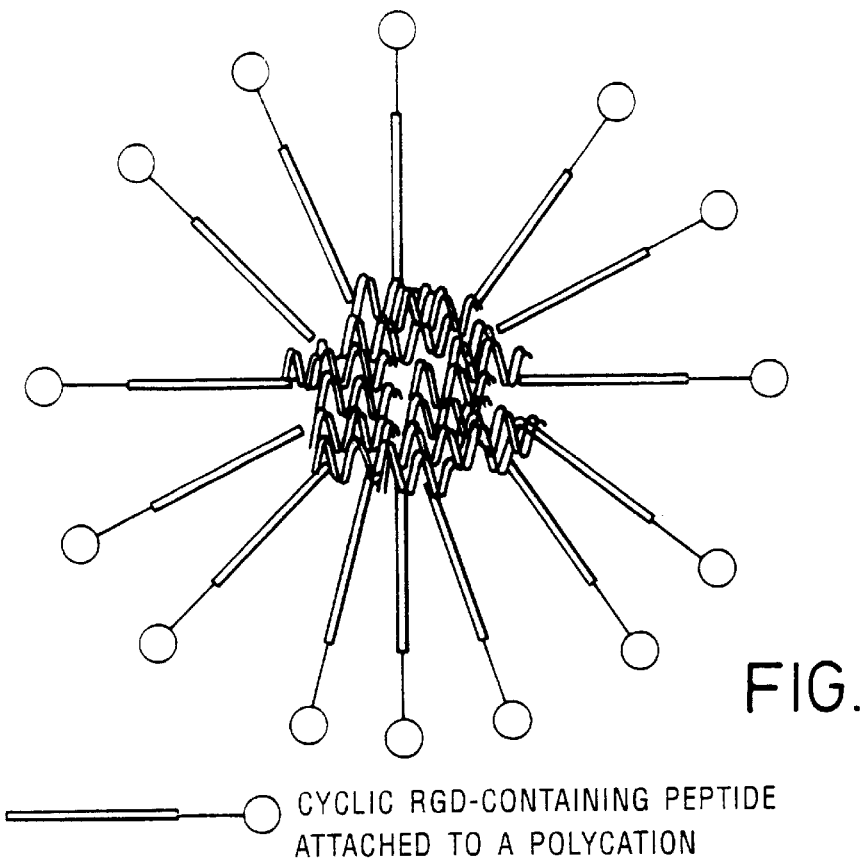
FIG. 1: shows a possible structure for the polycation-integrin receptor binding moiety/DNA complex.

The approach taken by the present inventors is to use specific cell-surface integrin receptor binding moieties coupled to a polycation moiety which will bind to DNA.

The "DNA packages" will then bind to cell surface receptors and be internalised. It is also surprisingly been found that such an approach results in efficient expression of DNA so internalised, without the need for any co-factors or co-treatment. Nevertheless, co-factors can be used where desired. A preferred co-factor is chloroquine or any other factor which reduces endosomal degradative activity. The observation of improved expression in the presence of chloroquine may be because the peptide-DNA complex is internalised, at least in part, to endosomal compartments. Chloroquine is a weak buffer which is purported to prevent acidification of endosomal vesicles which limits the activity of endosomal degradative enzymes. Thus the internalised peptide-DNA complex has more opportunity to escape the endosome and avoid degradation. Other factors which might have a similar beneficial effect include ammonium chloride, another weak buffer which works like chloroquine; fusogenic peptides related to the N-terminus of the HA protein of influenza virus which mediate active membrane disruption and inactivated adenovirus capsids which also disrupt the membrane of the endosome.

One advantage of integrin receptor mediated internalisation is that large particles can be internalised, e.g. whole cells.

Thus, in a first aspect, the present invention provides a composition comprising DNA associated with a polycation wherein the polycation is coupled to an integrin receptor binding moiety.

In the present invention, "DNA" means single or double stranded DNA, either as complete coding sequences or parts thereof and, in particular, refers to coding sequences for one or more genes.

"Integrin receptor binding moiety" means any moiety or species capable of specifically binding to integrin receptors found on the surface of cells. In particular, it refers to integrin receptor binding peptides capable of binding to integrin receptors.

"Association" of the DNA and the polycation occurs, for example, by virtue of charge-charge interaction, but other forms of association are equally applicable.

In a preferred embodiment, the integrin receptor binding moiety comprises a peptide, in particular a cyclic peptide, comprising the sequence RGD (SEQ ID NO:1). In a particularly preferred embodiment, the peptide comprises the sequence GGCRGDMFGC (SEQ ID NO:2). Cyclic configuration in this sequence is imposed by virtue of the presence of two cysteine residues which can form a disulphide bond.

The compositions of the present invention bind effectively to integrin receptors found on cell surfaces and are internalised. The DNA is then effectively expressed by the cell without the need for any other co-factors being present or the need for any co-treatment. Of course, co-factors or co-treatments can be used in conjunction with the present invention to boost expression levels even further.

The polycation moiety can be any suitable polycation capable of forming a complex with DNA. In particular polycations such as polylysine can be used. The number of residues in the polycation can vary from a relatively small number, up to quite long chains, or can be a mixture thereof. For example, polycations of from 3–1000, 3–500 or indeed 3–100 residues can be used. In particular, 10–16 cation residues are suitable, particularly 16. In one embodiment of the invention, therefore, the polycation consists of 10–16 polylysine residues, with 16 lysine residues being particularly preferred.

It is believed that the polycation "tails" of the compositions of the invention associate with the DNA to be delivered, effectively forming a "package" with the integrin receptor binding moieties on the outside. The DNA composition can then bind to an integrin receptor on the cell surface and be internalised. The polycation may then act to protect the DNA from the cell's internal enzyme systems, enabling it to be integrated in the cell's genome and thus expressed.

In a further aspect, the present invention provides a DNA binding composition comprising an integrin receptor binding moiety coupled to a polycation. Preferably the integrin binding moiety is a peptide, as described above. Here coupling may occur to the C-terminus or to the N-terminus of the peptide. In one preferred embodiment, the polycation is polylysine.

This composition can then simply be brought into contact with DNA to "package" the DNA for delivery to a designated cell.

As discussed herein, compositions of the present invention enable the effective delivery of DNA to cells wherein it is internalised and expressed efficiently. In this way, genetic deficiencies of particular cell types can be overcome by the delivery and expression of DNA sequences encoding correct or "native" proteins. One example where such an approach may be effective is in the treatment of cystic fibrosis. Thus, in other aspects, the present invention provides:

(a) the use of a composition of the invention in the manufacture of a medicament for the treatment of prophylaxis of a condition related to a genetic deficiency or modification;

(b) a composition of the invention for use in the treatment or prophylaxis of a condition related to a genetic deficiency or modification;

(c) a method for the treatment or prophylaxis of a condition related to a genetic deficiency comprising the step of administering to a subject a composition of the invention;

(d) a method for the transformation of a host cell comprising the step of bringing together the cell with a composition of the invention; such methods find use generally in transfection of cells, particularly mammalian cells;

(e) the use of a composition of the invention in the preparation of a medicament for the treatment or prophylaxis of a condition caused by a genetic deficiency or modification; and (f) a pharmaceutical formulation comprising a composition of the invention together with one or more pharmaceutically acceptable carriers, diluents or excipients.

Preferred features of each aspect of the invention are as for each other aspect mutatis mutandis.

The invention will now be described by reference to the following examples.

EXAMPLE 1

Preparation of a First Polylysine-Integrin Receptor Binding Peptide

The peptide sequence GGCRGDMFGC(K)$_{16}$ (SEQ ID NO:3) was synthesised as follows:

(a) the peptide was synthesised on ABI model 431A solid-phase batch peptide synthesiser using Wang HMP resin and FMOC-cleavage strategy;

(b) the linear peptide was cleaved from the resin using 5 ml of a scavenger mixture (0.75 g phenol, 0.25 ml EDT, 0.5 ml thioanisole, 0.5 ml deionised $H_2O$, 10 ml TFA), the mixture was stirred for 2 hrs at room temperature and was then filtered over sinter into ice-cold MTBE. This was then stored at −18° C. before being spun down, washed with 3×6 ml MTBE before being dried in vacuo and redissolved in $H_2O$ and freeze dried;

(c) cyclisation of the peptide was carried out in 5% AcOH/20% DMSO v/v, buffered to pH 6 by 0.88 NH$_3$ (aq), with stirring for 24 hrs at room temperature. Finally, it was diluted (×3) using deionised water;

(d) purification by ion-exchange chromatography was carried out using mono-S resin, 50 mM HEPES buffer (pH 7.6) on Pharmacia FPLC system (monitored at 280 nm/UV-Hg lamp);

(e) fractions were assayed for effects on cell cultures;

(f) positive fractions were desalted using P2 Biogel and 0.1% aq TFA; and (g) further desalting was carried out using reverse-phase chromatography and 0.1% aq TFA on an FPLC system (monitored at 214 nm/Zn lamp).

EXAMPLE 2

Internalisation and Expression of a Reporter Gene Using the Polylysine-Integrin Receptor Binding Peptide Described in Example 1

Figure 2:
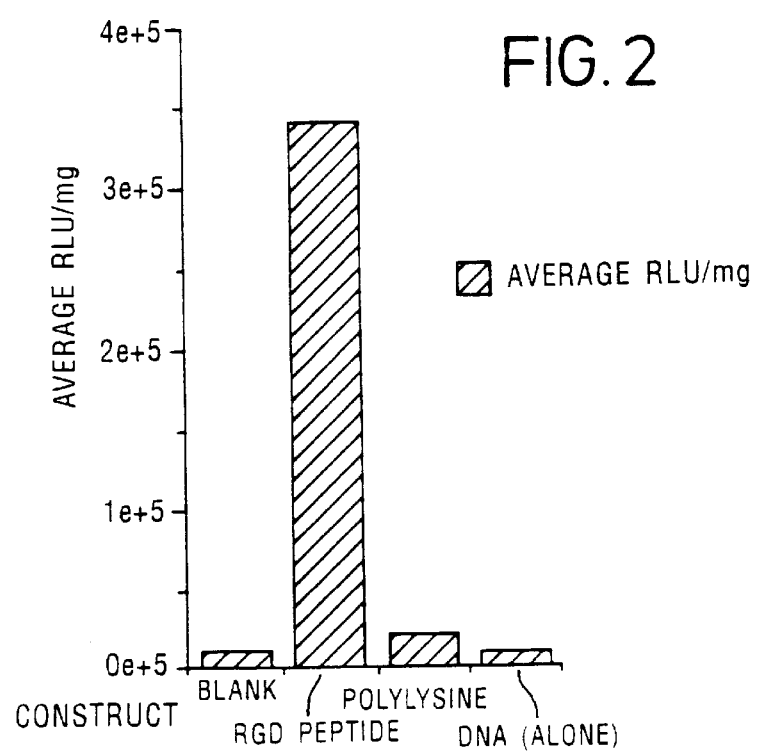
FIG. 2: shows levels of expression of a luciferase reporter protein in cells transformed with a composition of the invention, compared to suitable controls.

5 μg of a luciferase reporter gene plasmid (pGL2 promega) was complexed with either the RGD-polylysine construct (possible structure of complex is shown in FIG. 1) or an equal concentration of polylysine in 100 μl of Optimem media (Gibco). The DNA/peptide complexes and also a DNA only control were then applied to 50% confluent cultured (Caco-2) colonic epithelial cells which were then allowed to express for 48 hours. The cells were then harvested and the cellular protein analysed for luciferase activity (Relative Light Units). The activity shown in FIG. 2 is adjusted to represent activity from 1 mg of cellular protein. In FIG. 2 the term "RGD peptide" is used to indicate the polylysine-integrin receptor binding protein described in Example 1.

EXAMPLE 3

Preparation of a Second Polylysine-Integrin Receptor Binding Peptide

The peptide sequence (K)$_{16}$GGCRGDMFGCA (SEQ ID NO:4) was synthesised. This can be done using analogous techniques to those used in respect of Example 1. This peptide has a similar sequence to that referred to in Example 1, the main difference being that the polylysine region was present at the N-terminus rather than the C-terminus.

EXAMPLE 4

Internalisation and Expression of Reporter Gene Using the Polylysine-Integrin Receptor Binding Peptide Described in Example 3

Figure 3:
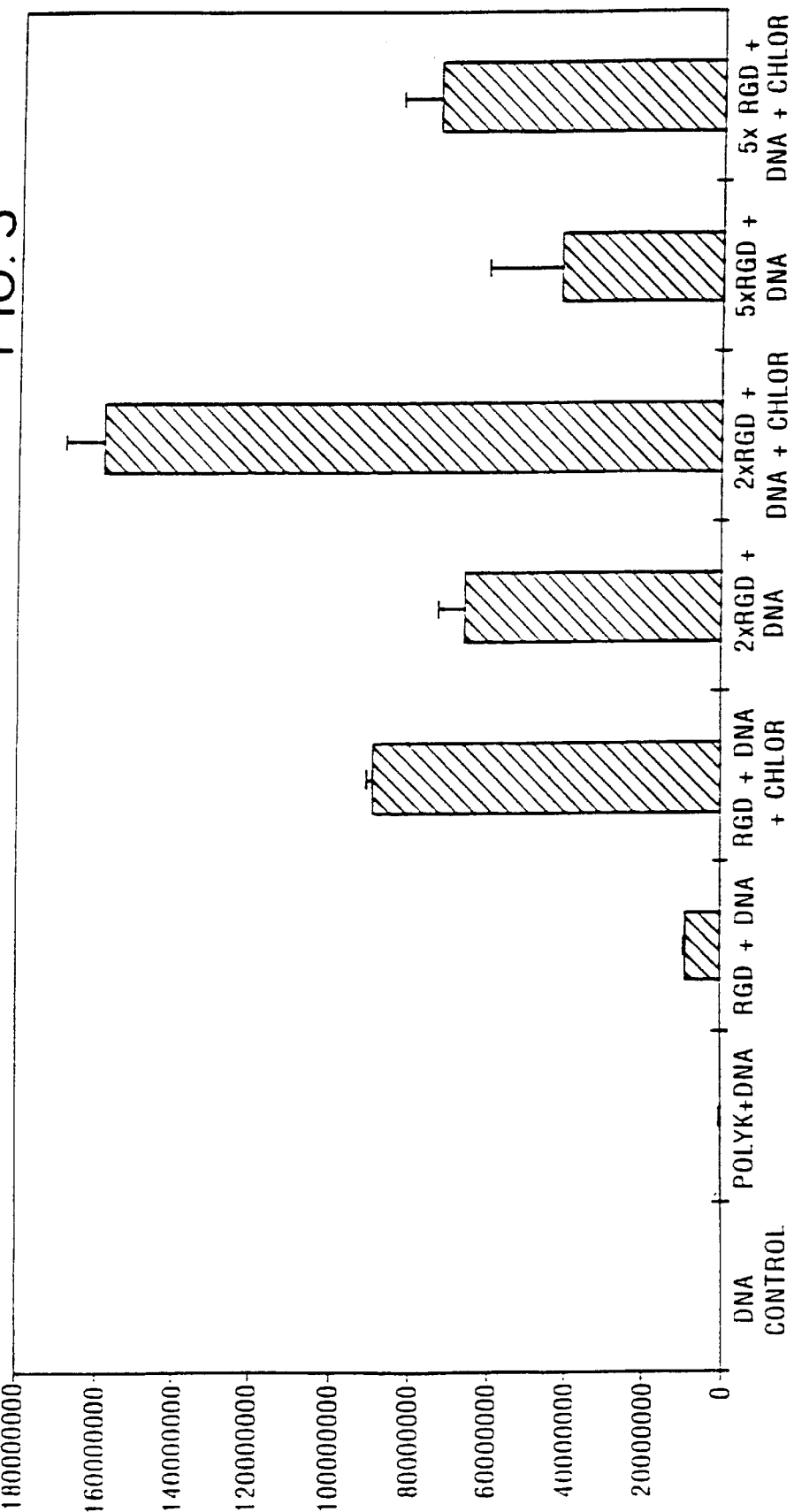
FIG. 3: also shows levels of expression of a luciferase reporter protein in cells with a composition of the present invention, compared to suitable controls, but here the composition is different from that used in respect of FIG. 2.

The procedure described in Example 2 was repeated but using the polylysine-integrin receptor binding peptide described in Example 3 instead of the polylysine-integrin receptor binding peptide described in Example 1. Control experiments were also performed. The results are shown in FIG. 3, wherein:

DNA control=5 μg of PGL2 plasmid DNA

PolyK=poly-L-lysine

RGD=newly synthesised RGD-containing peptide linked to polylysine (described in Example 3)

Chlor=100 μM chloroquine

2×RGD+DNA=twice as much as peptide, DNA same (5 μg)

5×RGD+DNA=five times as much peptide.

An indirect comparison of optimal peptide-DNA transfection efficiencies in the absence of chloroquine suggests that the peptide prepared in Example 3 (±6×10$^7$ RLU/mg) is more efficient than the peptide prepared in Example 1 (±3.5×10$^5$ RLU/mg in FIG. 2) at delivery and expression of the luciferase reporter gene. The addition of chloroquine improved expression a further 2 fold approximately, suggesting that endosomal degradation is limiting the expression levels somewhat. It is interesting in comparison, however, that, in some circumstances, the efficiency of the transferrin-polylysine receptor-mediated gene delivery system was improved by more than 1,000-fold in the presence of chloroquine. The high level of expression by the RGD-polylysine peptide without co-factors and the relatively small improvement in enhancement with chloroquine is surprising.

EXAMPLE 5

Transfection of Caco-2 Cells with K16 RGD Peptide and Effect of Chloroquine

Figure 4:
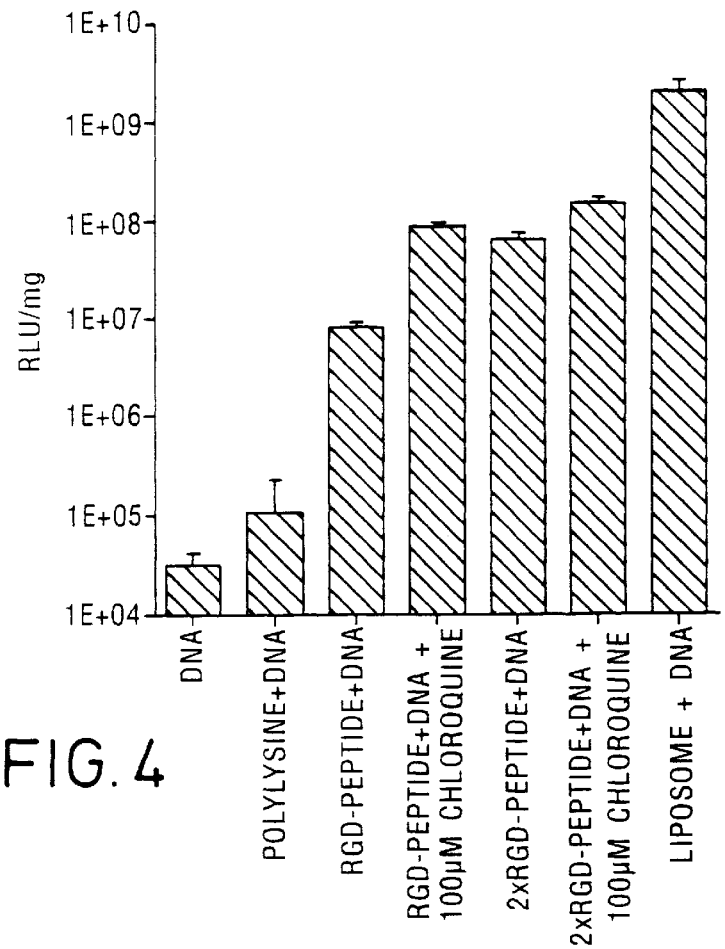
FIG. 4: shows levels of expression of a luciferase reporter protein in cells transformed with various compositions of the invention.

The polylysine-integrin receptor binding peptide of Example 1 was used in a repeat of the procedure of Example 2, but using 1 μg of luciferase reporter gene plasmid. The effect of chloroquine was also investigated. The results are shown in FIG. 4. Highest transfection levels were achieved with 2×RGD peptide and 100 nm chloroquine, these transfection levels being approximately 10-fold lower than those achieved with lipofectamine. It can again be seen that chloroquine gave a relatively small improvement with 2×RGD peptide+DNA, although with RGD-peptide+DNA the improvement was greater.

EXAMPLE 6

Effects of Chloroquine on Transfection of COS-7 cells with RGD peptides

Figure 5:
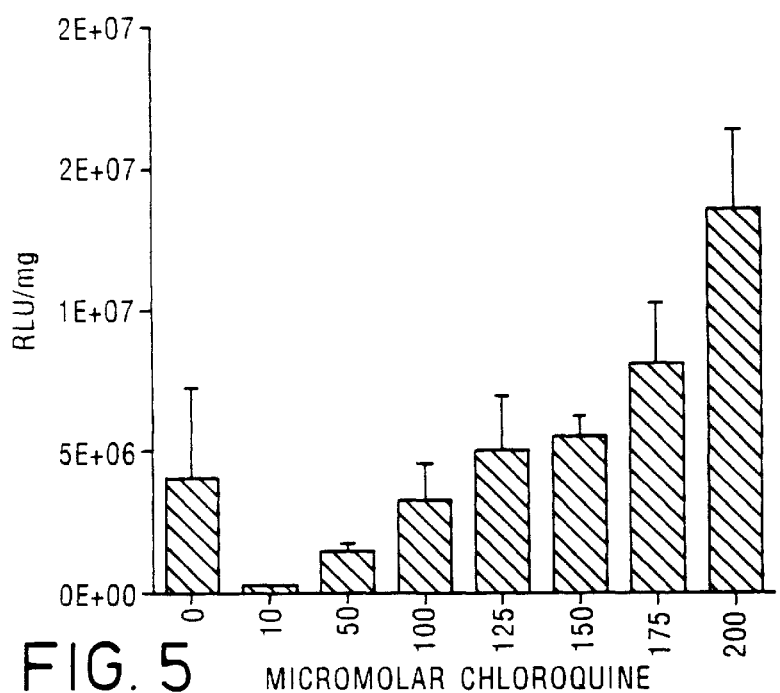
FIG. 5: shows the effect of chloroquine on expression of a luciferase reporter protein in COS-7 cells.

The polylysine-integrin receptor binding peptide of Example 1 was again used. Essentially the methodology of Example 2 was followed with the substitution of COS-7 cells, and the use of different concentrations of chloroquine. The results are shown in FIG. 5. It can be seen that 200 μm chloroquine gave a 4-fold increase of expression, compared with no chloroquine. However, at these levels, cytopathic effects of chloroquine were apparent.

EXAMPLE 7

Effects of Chloroquine on Transfection of Endothelial Cells with RGD Peptides

Figure 6:
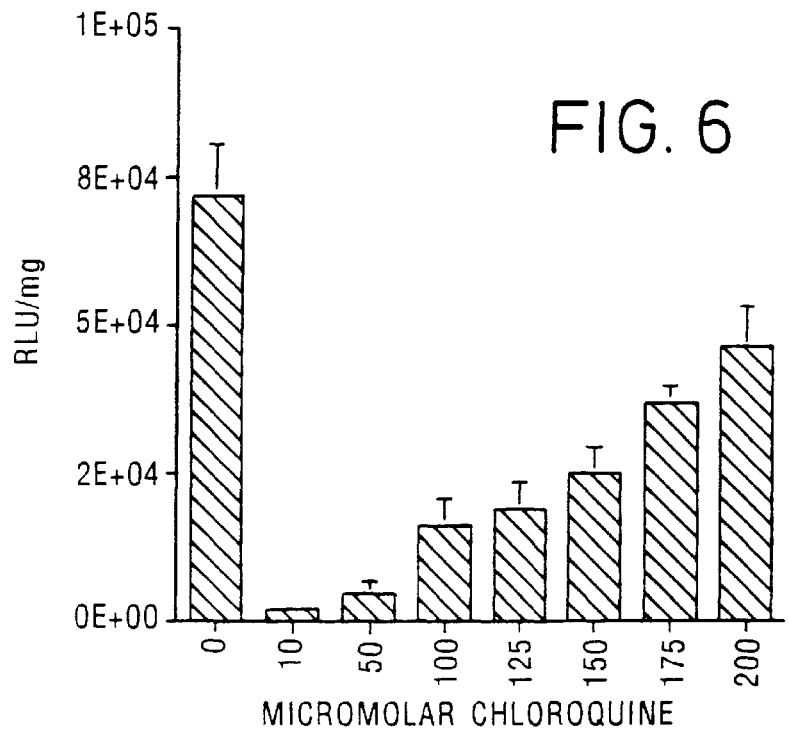
FIG. 6: shows the effect of chloroquine on expression of a luciferase reporter protein in endothelial cells.

This was a repeat of Example 6 using ECV 304 endothelial cells. The results are shown in FIG. 6. For these cells, the highest level of expression was obtained in the absence of chloroquine. Although increasing levels of chloroquine restored expression to some extent, complete restoration was not achieved.

EXAMPLE 8

Transfection of COS-7 cells with RGD-Polylysine Peptides

Figure 7:
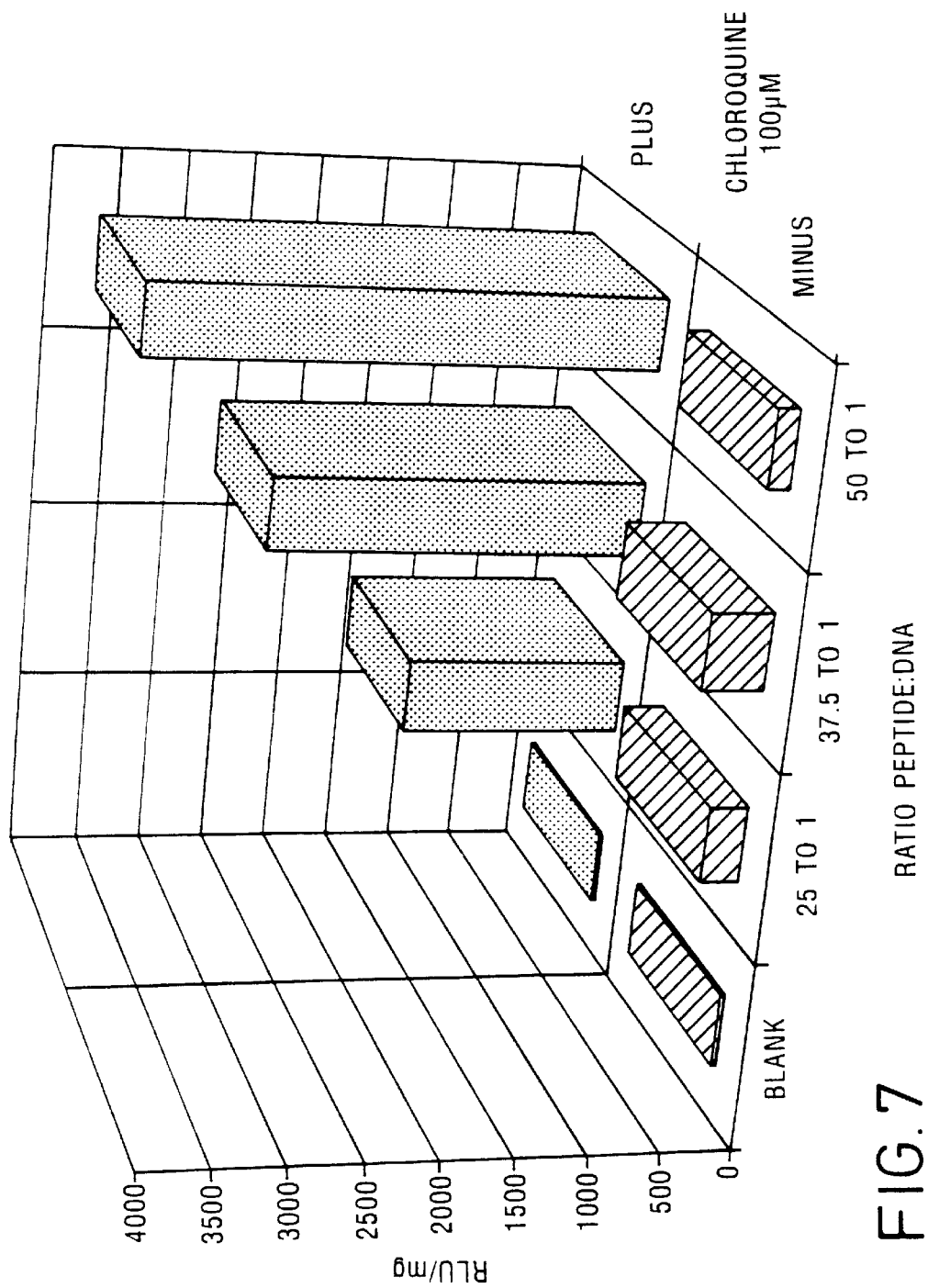
FIG. 7: shows the results of expression of a luciferase reporter protein in COS-7 cells using differing ratios of RGD peptide:DNA, in the presence and absence of chloroquine.

The methodology of Example 2 was repeated using COS-7 cells. In this experiment, different ratios of the K16 RGD peptide DNA were used with and without 100 μm chloroquine, with the results shown in FIG. 7. It can be seen that the optimum ratio was 37.5:1 in both the absence and presence of chloroquine.

EXAMPLE 9

Transfection of Endothelial Cells with RGD-Polylysine Peptides

Figure 8:
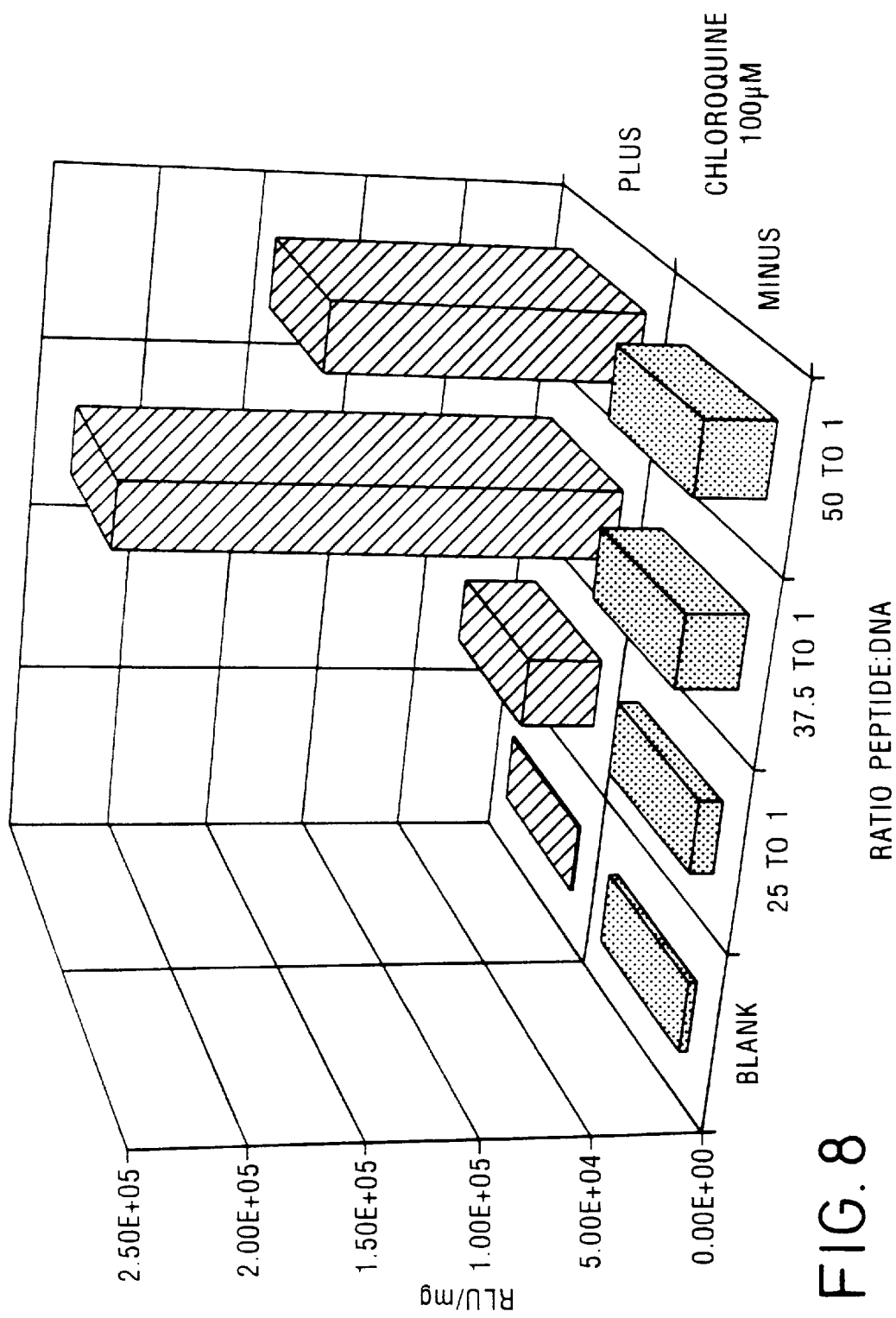
FIG. 8: shows the results of expression of a luciferase reporter protein in endothelial cells using differing ratios of RGD peptide:DNA, in the presence and absence of chloroquine.

This was a repeat of Example 8 using ECV 304 endothelial cells. The results are shown in FIG. 8.

EXAMPLE 10

Figure 9:
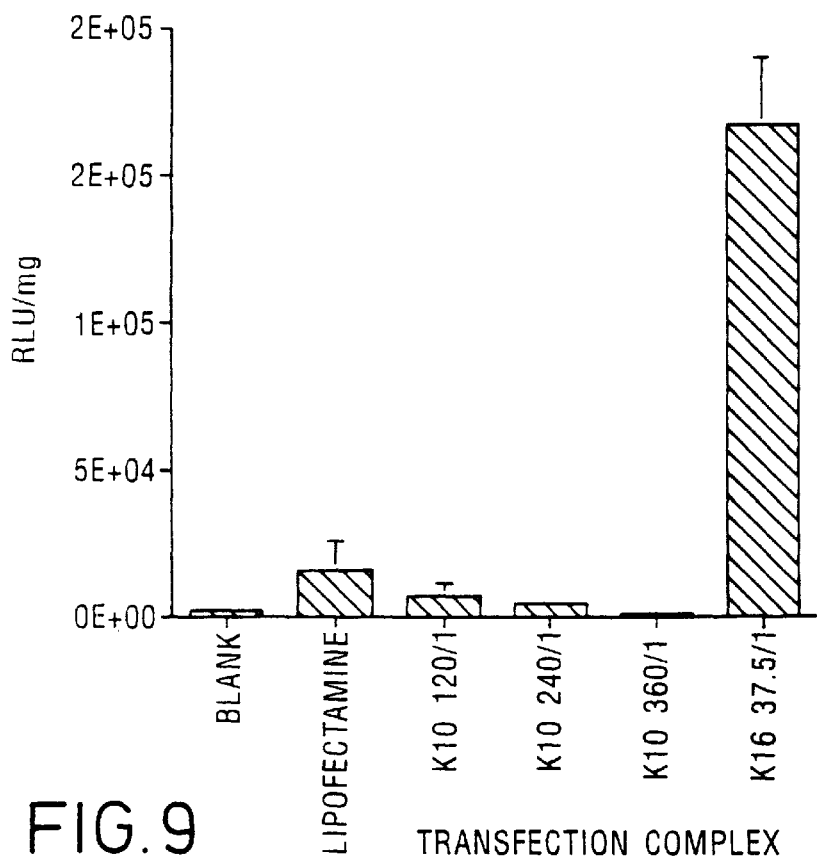
FIG. 9: shows the results of comparing transfection of endothelial cells with varying ratios of K10 peptide:DNA and of K16 peptide:DNA.

Transfection of Endothelial Cells Comparing K10 and K16 RGD Peptides with Lipofectamine ECV 304 endothelial cells were transfected with the optimised ratio of K16 RGD peptide-DNA complex (37.5:1) derived from Example 9. In addition, a range of ratios of K10 RGD peptide-DNA complex were also investigated, as well as transfection using lipofectamine. The results are shown in FIG. 9, with the optimised K16 RGD-DNA complex beingz the most efficient.

---

We claim:

1. A composition comprising DNA which encodes a peptide or protein, said DNA being operatively linked to a transcriptional regulatory sequence and said DNA being associated with a polycation consisting of 3–100 lysine residues wherein the polycation is itself coupled to an integrin receptor binding protein or peptide.

2. The composition as claimed in claim 1 wherein the integrin receptor binding protein or peptide is a peptide.

3. The composition of claim 1 wherein said integrin receptor binding protein or peptide is a peptide which comprises a sequence which comprises the amino acid sequence RGD, SEQ ID NO. 1.

4. The composition as claimed in claim 1 wherein the integrin receptor binding peptide or protein comprises the amino acid sequence RGD, SEQ ID NO. 1.

5. The composition as claimed in claim 1 wherein the integrin receptor binding peptide or protein is cyclic.

6. The composition as claimed in claim 5 wherein the integrin receptor binding peptide or protein comprises at least two cysteine residues capable of forming a disulphide bond.

7. The composition as claimed in claim 6 wherein the integrin receptor binding peptide or protein comprises the amino acid sequence GGCRGDMFGC, SEQ ID NO. 2.

8. The composition as claimed in claim 1, wherein the polycation consists of 10–16 cation residues.

9. The composition as claimed in claim 8 wherein the polycation consists of 16 cation residues.

10. The composition as claimed in claim 9 wherein the ratio of polycation to DNA is 37.5:1.

11. The composition as claimed in claim 1 wherein the DNA is double stranded.

12. The composition of claim 1 wherein said DNA encodes a gene.

13. The composition as claimed in claim 11 wherein the DNA comprises one or more complete gene coding sequences.

14. The composition as claimed in claim 13 wherein the DNA includes the coding sequence of the cystic fibrosis gene.

15. The composition according to claim 1, further comprising a factor which reduces endosomal degradative activity.

16. A DNA binding composition comprising a polycation consisting of 3–100 lysine residues coupled to an integrin receptor binding protein or peptide.

17. The composition as claimed in claim 16 wherein the integrin receptor binding protein or peptide is a peptide.

18. The composition as claimed in claim 16 wherein the integrin receptor binding peptide or protein comprises the amino acid sequence RGD, SEQ ID NO.1.

19. The composition as claimed in claim 16 wherein the integrin receptor binding peptide or protein is cyclic.

20. The composition as claimed in claim 16 wherein the integrin receptor binding peptide or protein comprises at least two cysteine residues capable of forming a disulphide bond.

21. The composition as claimed in claim 20 wherein the integrin receptor binding peptide or protein comprises the amino acid sequence GGCRGDMFGC, SEQ ID NO. 2.

22. The composition as claimed in claim 16 wherein the polycation consists of 10–16 cation residues.

23. The composition as claimed in claim 22 wherein the polycation consists of 16 cation residues.

24. A method of preparing a composition as defined in claim 1 which comprises the step of combining said DNA with a DNA binding composition, said DNA binding composition comprising a polycation consisting of 3–100 lysine residues coupled to an integrin receptor binding protein or peptide.

25. The method as claimed in claim 24 wherein the DNA is double stranded DNA.

26. The method of claim 24 wherein the DNA comprises one or more complete gene coding sequences.

27. The method of claim 24 wherein the DNA comprises the coding sequence of the cystic fibrosis gene.

28. A method of expressing DNA which encodes a peptide or protein in a host cell which comprises the step of combining in vitro the host cell and a composition as defined in claim 1.

29. The method as claimed in claim 28 wherein the host cell is a mammalian cell.

30. A method for preparing the composition as defined in claim 16 comprising the steps of:

(a) synthesising an integrin receptor binding protein or peptide coupled to a polycation consisting of 3–100 lysine residues;

(b) subjecting the integrin receptor binding protein or peptide to a cyclisation step;

(c) purifying the mixture of peptides obtained by ion-exchange chromatography;

(d) assaying fractions for presence of integrin receptor binding protein or peptide;

(e) desalting fractions containing integrin receptor binding protein or peptide; and (f) further desalting the integrin receptor binding protein or peptide containing fractions using reverse phase chromatography.

* * * * *